(12) United States Patent
Kaspar et al.

(10) Patent No.: US 10,172,789 B2
(45) Date of Patent: Jan. 8, 2019

(54) COMPOSITIONS FOR TRANSDERMAL DELIVERY OF MTOR INHIBITORS

(71) Applicant: PALVELLA THERAPEUTICS LLC, Wayne, PA (US)

(72) Inventors: Roger L. Kaspar, Santa Cruz, CA (US); Tycho Speaker, Santa Cruz, CA (US)

(73) Assignee: PALVELLA THERAPEUTICS LLC, Wayne, PA (US)

( * ) Notice: Subject to any disclaimer, the term of this patent is extended or adjusted under 35 U.S.C. 154(b) by 0 days.

(21) Appl. No.: 14/164,056

(22) Filed: Jan. 24, 2014

(65) Prior Publication Data

US 2014/0315942 A1 Oct. 23, 2014

Related U.S. Application Data

(60) Provisional application No. 61/756,406, filed on Jan. 24, 2013.

(51) Int. Cl.
*A61K 9/00* (2006.01)
*A61K 31/436* (2006.01)
*A61K 47/10* (2017.01)
*A61K 47/12* (2006.01)
*A61K 47/32* (2006.01)
*C07D 498/18* (2006.01)

(52) U.S. Cl.
CPC .......... *A61K 9/0014* (2013.01); *A61K 31/436* (2013.01); *A61K 47/10* (2013.01); *A61K 47/12* (2013.01); *A61K 47/32* (2013.01); *C07D 498/18* (2013.01)

(58) Field of Classification Search
None
See application file for complete search history.

(56) References Cited

U.S. PATENT DOCUMENTS

| 5,286,730 A | 2/1994 | Caufield et al. |
| 5,540,931 A | 7/1996 | Hewitt et al. |
| 5,578,609 A | 11/1996 | Batt et al. |

(Continued)

FOREIGN PATENT DOCUMENTS

| CA | 2317010 A1 | 7/1997 |
| CA | 2825786 A1 | 9/2012 |

(Continued)

OTHER PUBLICATIONS

Hickerson et al.; "Rapamycin selectively inhibits expression of an inducible keratin (K6a) in human keratinocytes and improves symptoms in pachyonychia congenita patients;" Journal of Dermatological Science (2009), vol. 56, pp. 82-88; Elsevier Ireland Ltd.

(Continued)

*Primary Examiner* — Bethany P Barham
*Assistant Examiner* — Barbara S Frazier
(74) *Attorney, Agent, or Firm* — Pepper Hamilton LLP

(57) ABSTRACT

The present invention is drawn to formulations for the transdermal delivery of rapamycin or other related compounds. Specifically, in one embodiment a formulation for transdermally delivering rapamycin includes an mTOR inhibitor, such as rapamycin, water, a polymer having surfactant properties, a polymer having thickening properties, a solvent for solubilizing the mTOR inhibitor, a glycol, a $C_{10}$-$C_{20}$ fatty acid; and a base.

30 Claims, 3 Drawing Sheets

(56) References Cited

U.S. PATENT DOCUMENTS

Figure 1:
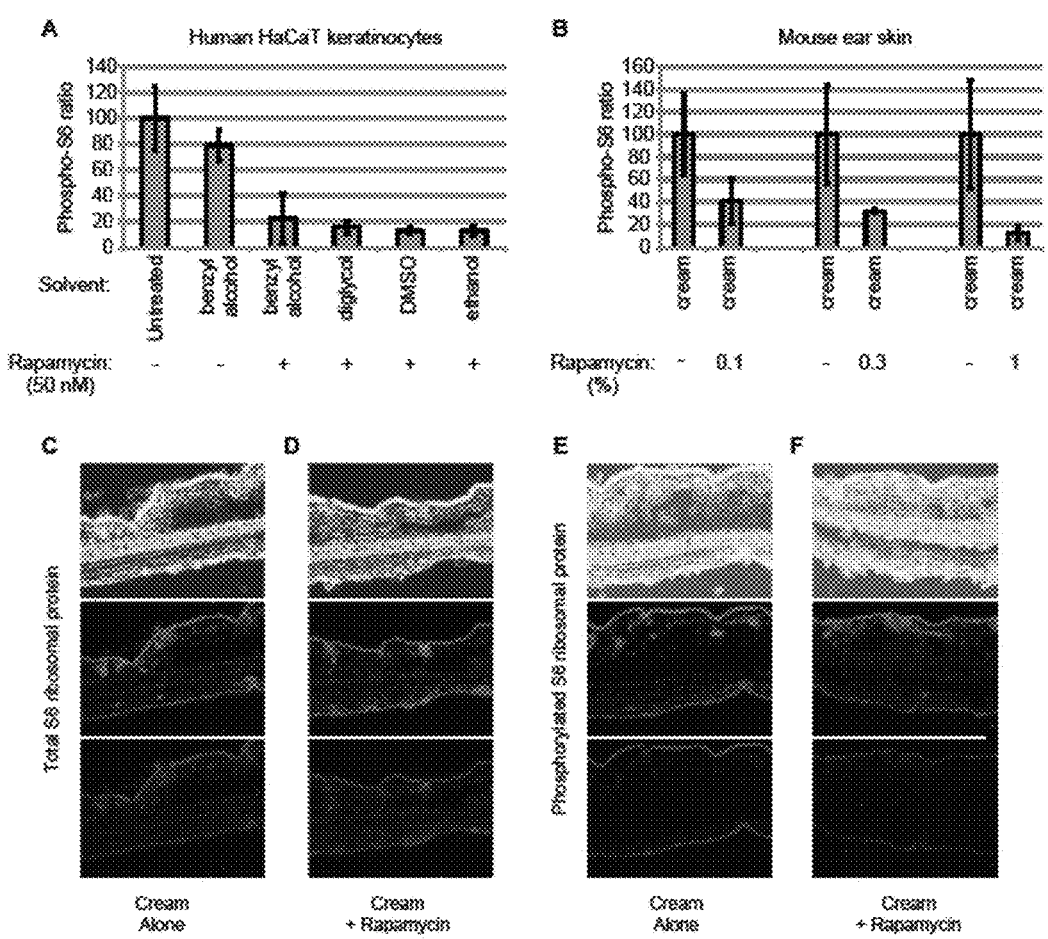

| | | |
|---|---|---|
| 5,631,282 A | 5/1997 | Goetz |
| 5,646,160 A | 7/1997 | Morris et al. |
| 5,670,504 A | 9/1997 | Bochis et al. |
| 5,939,427 A | 8/1999 | Kagayama et al. |
| 5,994,081 A | 11/1999 | Tang et al. |
| 6,110,910 A | 8/2000 | Magolda et al. |
| 6,197,829 B1 | 3/2001 | Fujii et al. |
| 6,221,843 B1 | 4/2001 | Tang et al. |
| 6,352,998 B2 | 3/2002 | Jackman et al. |
| 6,455,518 B2 | 9/2002 | Zenke et al. |
| 6,958,153 B1 | 10/2005 | Ormerod et al. |
| 7,083,802 B2 | 8/2006 | Peyman |
| 7,169,594 B2 | 1/2007 | Guan |
| 7,345,053 B2 | 3/2008 | Garvey |
| 7,416,724 B2 | 8/2008 | Guan |
| 7,534,808 B2 | 5/2009 | Evenou et al. |
| 7,566,718 B2 | 7/2009 | Wong et al. |
| 7,758,886 B2 | 7/2010 | Jauernig et al. |
| 7,763,616 B2 | 7/2010 | Yu et al. |
| 7,776,862 B2 | 8/2010 | McGuinness et al. |
| 7,781,437 B2 | 8/2010 | Kim et al. |
| 7,799,789 B2 | 9/2010 | Anilkumar et al. |
| 7,868,005 B2 | 1/2011 | Rosenblum et al. |
| 7,879,838 B2 | 2/2011 | Zeng et al. |
| 7,985,415 B2 | 7/2011 | Giroux |
| 8,114,385 B2 | 2/2012 | Tamarkin et al. |
| 8,207,170 B2 | 6/2012 | Kim et al. |
| 8,221,752 B2 | 7/2012 | Kasaian et al. |
| 8,367,606 B2 | 2/2013 | Tennenbaum et al. |
| 8,372,434 B2 | 2/2013 | Bague et al. |
| 8,435,544 B2 | 5/2013 | Mitra et al. |
| 8,454,945 B2 | 6/2013 | McCook et al. |
| 8,574,562 B2 | 11/2013 | Goebel |
| 8,614,178 B2 | 12/2013 | Theisinger et al. |
| 8,617,598 B2 | 12/2013 | Haeberlin et al. |
| 8,623,833 B2 | 1/2014 | Rothbard et al. |
| 8,663,639 B2 | 3/2014 | Dor et al. |
| 8,715,741 B2 | 5/2014 | Maitra et al. |
| 8,911,786 B2 | 12/2014 | Desai et al. |
| 8,946,256 B2 | 2/2015 | Bacus |
| 9,011,915 B2 | 4/2015 | Wong et al. |
| 9,034,881 B2 | 5/2015 | Magilavy |
| 9,169,269 B2 | 10/2015 | Mangia et al. |
| 9,173,841 B2 | 11/2015 | Kang et al. |
| 9,308,262 B2 | 4/2016 | Gunther et al. |
| 9,346,836 B2 | 5/2016 | Morgan |
| 9,360,471 B2 | 6/2016 | Qi |
| 9,447,184 B2 | 9/2016 | Wu et al. |
| 9,522,146 B2 | 12/2016 | Ren et al. |
| 9,526,723 B2 | 12/2016 | Moss et al. |
| 9,549,929 B2 | 1/2017 | Brown et al. |
| 9,549,966 B2 | 1/2017 | Hamrah et al. |
| 9,757,459 B2 | 9/2017 | Theisinger et al. |
| 2001/0031769 A1 | 10/2001 | Jackman et al. |
| 2002/0015702 A1 | 2/2002 | Burkly et al. |
| 2002/0016625 A1 | 2/2002 | Falotico et al. |
| 2003/0170630 A1 | 9/2003 | Alsobrook, II et al. |
| 2005/0031547 A1 | 2/2005 | Temarkin et al. |
| 2005/0090553 A1 | 4/2005 | Shapiro |
| 2005/0192261 A1 | 9/2005 | Jost-Price et al. |
| 2005/0220850 A1 | 10/2005 | Ledergerber et al. |
| 2005/0249757 A1 | 11/2005 | Kannan et al. |
| 2005/0250804 A1 | 11/2005 | Kannan et al. |
| 2005/0250805 A1 | 11/2005 | Kannan et al. |
| 2006/0035907 A1 | 2/2006 | Christensen et al. |
| 2006/0128739 A1 | 6/2006 | Maryanoff et al. |
| 2006/0154952 A1 | 7/2006 | Moore |
| 2006/0194769 A1 | 8/2006 | Johnson et al. |
| 2006/0210604 A1 | 9/2006 | Dadey et al. |
| 2006/0210638 A1 | 9/2006 | Liversridge et al. |
| 2006/0228394 A1 | 10/2006 | Peyman |
| 2007/0031509 A1 | 2/2007 | Sundae |
| 2007/0203171 A1 | 8/2007 | Zhao |
| 2007/0219271 A1 | 9/2007 | Mittmann et al. |
| 2008/0009437 A1 | 1/2008 | Kia et al. |
| 2008/0064668 A1 | 3/2008 | Uskokovic et al. |
| 2008/0124400 A1 | 5/2008 | Liggins et al. |
| 2008/0207670 A1 | 8/2008 | Sirinyan et al. |
| 2008/0207672 A1 | 8/2008 | Kaspar et al. |
| 2008/0299220 A1 | 12/2008 | Tamarkin et al. |
| 2009/0022774 A1 | 1/2009 | Mollison et al. |
| 2009/0088373 A1 | 4/2009 | Gallo et al. |
| 2009/0130029 A1 | 5/2009 | Tamarkin et al. |
| 2009/0226430 A1 | 9/2009 | Hanna et al. |
| 2010/0081681 A1 | 4/2010 | Blagosklonny |
| 2010/0172993 A1 | 7/2010 | Singh et al. |
| 2010/0203103 A1 | 8/2010 | Dana et al. |
| 2012/0022095 A1 | 1/2012 | Teng et al. |
| 2013/0059795 A1 | 3/2013 | Lo et al. |
| 2013/0102572 A1 | 4/2013 | Sugarman |
| 2013/0225630 A1 | 8/2013 | Teng et al. |
| 2013/0225631 A1 | 8/2013 | Teng et al. |
| 2013/0317053 A1 | 11/2013 | Kaneda et al. |
| 2014/0079686 A1 | 3/2014 | Barman et al. |
| 2014/0100180 A1 | 4/2014 | Gunther et al. |
| 2014/0271871 A1 | 9/2014 | Desai et al. |
| 2015/0051242 A1 | 2/2015 | Zhao |
| 2015/0202187 A1 | 7/2015 | Bacus et al. |
| 2015/0238605 A1 | 8/2015 | Gunther et al. |
| 2015/0265582 A1 | 9/2015 | Armer et al. |
| 2015/0328193 A1 | 11/2015 | Henske et al. |
| 2015/0359900 A1 | 12/2015 | Wang et al. |
| 2016/0024101 A1 | 1/2016 | Elsner et al. |
| 2016/0120860 A1 | 5/2016 | Orlow et al. |
| 2016/0184279 A1 | 6/2016 | Kaspar et al. |
| 2016/0235668 A1 | 8/2016 | Rothberg et al. |
| 2016/0256443 A1 | 9/2016 | Kaspar et al. |
| 2016/0287611 A1 | 10/2016 | Dobak |
| 2016/0326168 A1 | 11/2016 | Ibrahim et al. |
| 2017/0009239 A1 | 1/2017 | Khvorova et al. |
| 2017/0014341 A1 | 1/2017 | Armer et al. |

FOREIGN PATENT DOCUMENTS

| | | |
|---|---|---|
| CA | 2941436 A1 | 12/2015 |
| EP | 0605161 A2 | 7/1994 |
| EP | 0703985 B1 | 10/2003 |
| EP | 1441696 B1 | 8/2004 |
| EP | 1147766 B1 | 7/2005 |
| EP | 1679064 A2 | 7/2006 |
| EP | 2033968 A1 | 3/2009 |
| EP | 2068932 B1 | 6/2009 |
| EP | 1933759 B1 | 12/2014 |
| EP | 2948134 A1 | 12/2015 |
| WO | 2000010516 A1 | 3/2000 |
| WO | 2005091891 A2 | 10/2005 |
| WO | 2006123226 A2 | 11/2006 |
| WO | 2008015539 A2 | 2/2008 |
| WO | 2008063563 A2 | 5/2008 |
| WO | 2009046436 A1 | 4/2009 |
| WO | 2014117035 A1 | 7/2014 |
| WO | 199024036 A1 | 9/2014 |
| WO | 2014132227 A1 | 9/2014 |
| WO | 2014177123 A1 | 11/2014 |
| WO | 2015121836 A1 | 8/2015 |
| WO | 2016071677 A1 | 5/2016 |
| WO | 2016094732 A1 | 6/2016 |
| WO | 2016124601 A1 | 8/2016 |
| WO | 2017053222 A1 | 3/2017 |

OTHER PUBLICATIONS

Ormerod et al.; "Treatment of psoriasis with topical sirolimus: preclinical development and a randomized, double-blind trial;" British Journal of Dermatology (2005), vol. 152, pp. 758-764; British Association of Dermatologists.

PCT Application No. PCT/US14/13066: Filing date Jan. 24, 2014; Transderm, Inc.; International Search Report dated May 7, 2014.

Ashton et al. "Prenatal Diagnosis for Inherited Skin Diseases" (2000) Clinics in Dermatology 18:643-648.

Avni et al. "Vertebrate mRNAs with a 5'-Terminal Pyrimidine Tract Are Candidates for Translation Repression in Quiescent Cells:

(56) References Cited

OTHER PUBLICATIONS

Characterization of the Translation cis-Regulatory Element" (Jun. 1994) Molecular and Cellular Biology 14(6):3822-3833.
Bowden et al. "Mutation of a type II keratin gene (K6a) in pachyonychia congenita" (Jul. 1995) Nat. Genet. 10:363-365 (abstract only).
Hay et al. "Upstream and downstream of mTOR" (2004) Genes & Development 18:1926-1945.
Hickerson et al. "SiRNA-Mediated Selective Inhibition of Mutant Keratin mRNAs Responsible for the Skin Disorder Pachyonychia Congenita" (Oct. 2006) Ann. N. Y. Acad. Sci. 1082:56-61.
International Search Report and Written Opinion for PCT/US2007/024077 dated May 29, 2008.
International Search Report and Written Opinion for PCT/US2015/065113 dated Mar. 4, 2016.
Jefferies et al. "Rapamycin selectively represses translation of the "polypyrimidine tract" mRNA family" (May 1994) PNAS USA 91:4441-4445.
Jefferies et al. "Rapamycin Suppresses 5'Top Mrna Translation Through Inhibition of P70s6k" (1997) The EMBO Journal 16(12):3693-3704.
Kaspar et al. "A Regulatory Cis Element and a Specific Binding Factor Involved in the Mitogenic Control of Murine Ribosomal Protein L32 Translation" (Jan. 5, 1992) The Journal of Biological Chemistry and Molecular Biology 267 (1):508-514.
Leigh et al "Keratins (K16 and K17) as markers of keratinocyte hyperproliferation in psoriasis in vivo and in vitro" (Oct. 1995) Br J Dermatology 133:501-511 (abstract only).
Macron "RNAi, startup believes siRNAs can treat extremely rare skin disorder" (Sep. 30, 2005) RNAi News 3 (36):4-5.
Meinert et al. "Clinical Trials Design, Conduct, and Analysis" (1986) Monographs in Epidemiology and Biostatistics , 8th ed. (abstract only).
Petroulakis et al. "mTOR signaling: implications for cancer and anticancer therapy" (2006) British Journal of Cancer 94:195-199.
Smith et al. "The Genetic Basis of Pachyonychia Congenita" (2005) J. Invest. Dermatol. Symp. Proc 10:21-30.
Supplemental European Search Report and Written Opinion for EP 14743123 dated Jul. 19, 2016.
Takahashi et al. "Cloning and Characterization of Multiple Human Genes and cDNAs Encoding Highly Related Type II Keratin 6 Isoforms" (Aug. 4, 1995) The Journal of Biological Chemistry 270(31):18581-18592 (NCBI Accession #L42584).
Terada et al. "Rapamycin selectively inhibits translation of mRNAs encoding elongation factors and ribosomal proteins" (Nov. 1994) PNAS USA 91:11477-11481.
Watson et al. "Sirolimus and Everolimus: Inhibitors of Mammalian Target of Rapamycin in Liver Transplantation" (2006) Transplantation Reviews 20:104-114.
Yonezawa "Identification of TOR-interacting Proteins" (Jun. 2003) Mol. Interv. 3(4):189-193.
Zhu "Differential translation of Top mRNA in rapamycin-treated human B lymphocytes" (May 2003) Dept. of Chemistry and Biochemistry, Brigham Young University, Provo, UT, USA (abstract only).
International Search Report and Written Opinion for PCT/US2018/012647 dated Mar. 13, 2018.

COMPOSITIONS FOR TRANSDERMAL DELIVERY OF MTOR INHIBITORS

PRIORITY DATA

This application claims the benefit of U.S. Provisional Patent Application Ser. No. 61/756,406, filed Jan. 24, 2013, which is incorporated herein by reference.

BACKGROUND

Rapamycin (Sirolimus) is a macrocyclic lactone that has been known for use as a pharmaceutically active agent for use in treating a variety of conditions. Various related compounds, such as temsirolimus, everolimus, torin-1, torin-2, WYE-354, and metformin show similar activity, suppressing the mammalian target of rapamycin (mTOR) biochemical pathway. RAPAMUNE®, an FDA approved dosage form, is an oral dosage form of rapamycin. However, there are some conditions for which oral rapamycin is ineffective and transdermal delivery of rapamycin and/or other mTOR inhibitors would be beneficial. Accordingly, research into transdermal delivery formulations for rapamycin is ongoing.

SUMMARY

The present invention is drawn to formulations for the transdermal delivery of mTOR inhibitors, such as rapamycin, and related methods of manufacture and use. Specifically, in one embodiment a formulation for transdermally delivering an mTOR inhibitor, such as rapamycin, may include an mTOR inhibitor a polymer having surfactant properties, a polymer having thickening properties, a solvent for solubilizing the mTOR inhibitor, a glycol, a $C_{10}$-$C_{20}$ fatty acid; and a base. The formulation may also include water for injection. In another embodiment, a formulation for transdermally delivering rapamycin can include about 55 wt % to about 98 wt % water, about 0.1 wt % to about 8 wt % rapamycin, about 0.05 wt % to about 1.0 wt % of a polymer having surfactant properties, about 0.4 wt % to about 1.0 wt % of a polymer having thickening properties, about 0.5 wt % to about 4.0 wt % of a glycol, about 1 wt % to about 40 wt % of benzyl alcohol, about 0.2 wt % to about 2.5 wt % of a $C_{10}$-$C_{20}$ fatty acid, and about 0.01 wt % to about 0.5 wt % of a base.

In a further embodiment, a method for transdermal administration of rapamycin is provided which includes the application of any of the rapamycin-containing formulations disclosed herein to a skin surface of a subject in need of rapamycin therapy.

BRIEF DESCRIPTIONS OF THE DRAWINGS

FIGS. 1A-F—FIG. 1A shows a plot of the effectiveness of rapamycin treatment on Human HaCaT keratinocytes when the rapamycin is dissolved in a variety of solvents. FIG. 1B shows a plot of the same measure when mouse ears were treated with placebo cream and a rapamycin containing cream. FIGS. 1C-F show immunochemistry (NC) images of frozen skin sections taken from mice treated with the same creams as FIG. 1B.

Figure 2A:
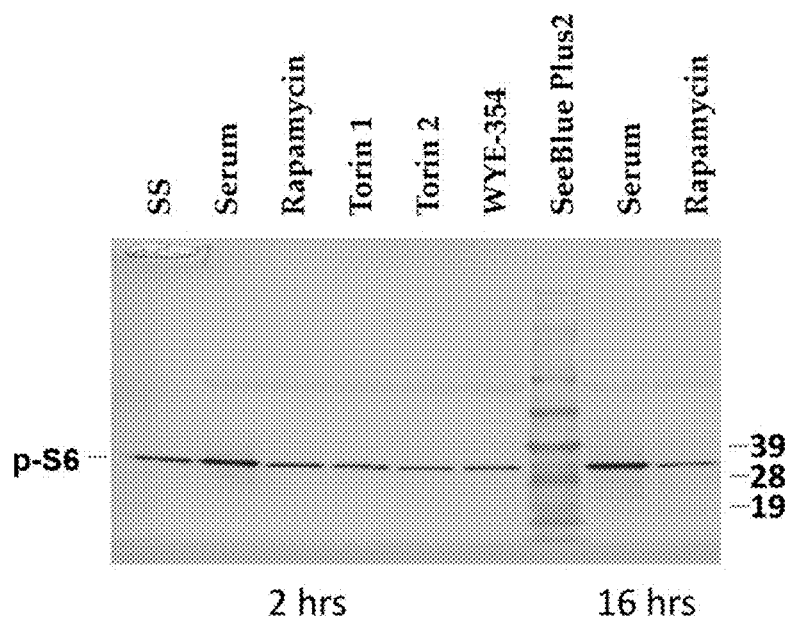
Figure 2B:
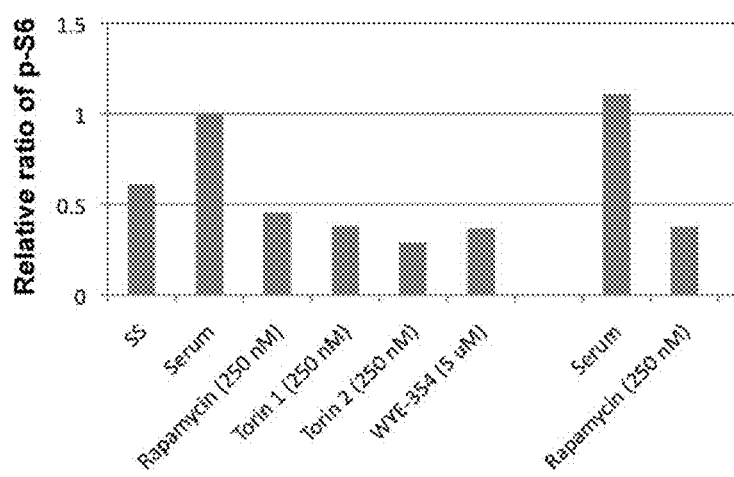

FIGS. 2A and B—FIG. 2A shows Western Blot analysis of Human HaCaT keratinocytes growing in serum ("Serum") that were treated with rapamycin or the other indicated mTOR inhibitors for the indicated times. FIG. 2B shows a plot of the p-S6 levels that were quantified and the ratio of p-S6 to total S6 (total S6 data not shown).

Figure 3:
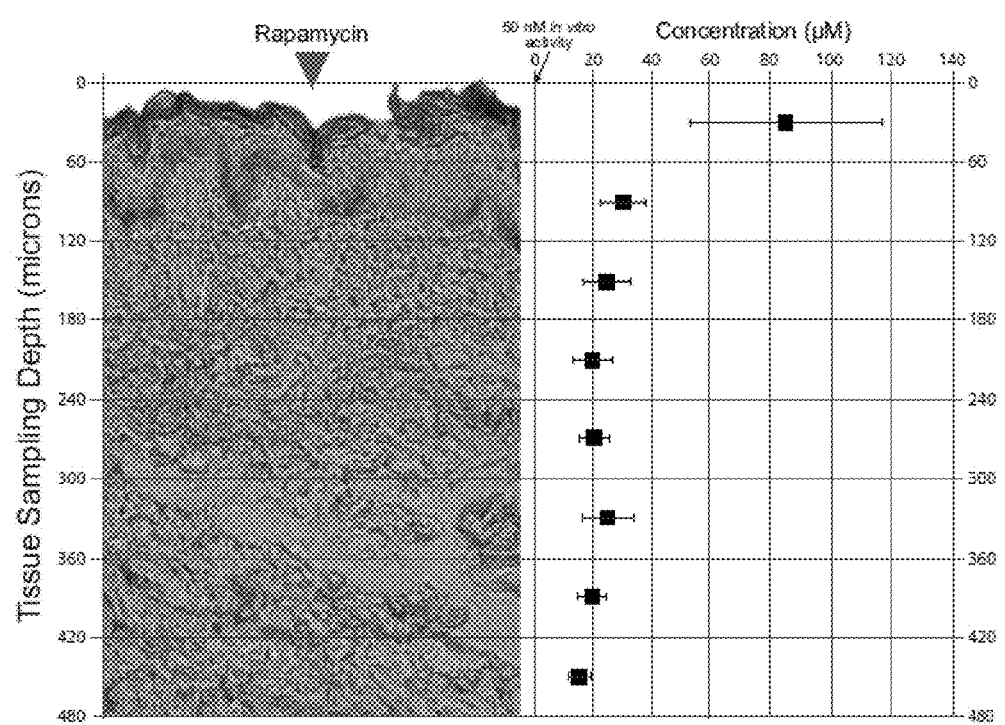

FIG. 3—shows rapamycin distribution in human explant skin 16 hours after application of a formulation in accordance with an embodiment of the present invention that contained rapamycin. Rapamycin extracted from the indicated tissue slices was assayed by reverse-phase HPLC. The tissue surface was cleaned with isopropyl alcohol prior to sectioning to remove any residual surface material. This formulation achieves rapamycin delivery to skin at levels many fold higher than required for in vitro activity. Overall, the net deposition of rapamycin within the skin was found to be in excess of 4% of the applied dose, indicating effective delivery.

DETAILED DESCRIPTION OF EXAMPLE EMBODIMENT(S)

Before the present oral dosage forms and methods for the delivery and use of rapamycin are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, "subject" refers to a mammal in having a condition for which rapamycin is a therapeutically effective treatment or preventative measure. In some aspects, such subject may be a human.

The term "mTOR inhibitor" refers to agents or compounds which are effective in inhibiting mTOR or an inhibitor of the mTOR signaling pathway. mTOR is a serine/threonine kinase that regulates translation and cell division. Examples of mTOR inhibitors include but are not limited to rapamycin (sirolimus) and its analogues and derivatives, temsirolimus, everolimus, the rapamycin prodrug AP-23573, AP-23481, the like, and combinations thereof.

As used herein, "rapamycin" or "sirolimus" are used interchangeably and refer to the macrocyclic lactone produced by the organism *Streptomyces hydroscopicus* isolated from soil samples of Easter Island (Rapa Nui) and having the structure of:

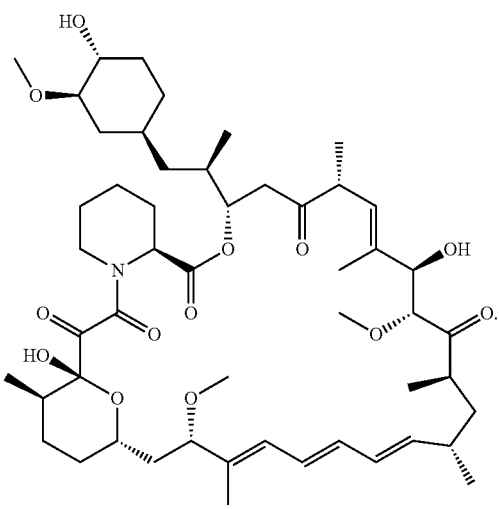 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

As used herein, "rapamycin and/or other mTOR inhibitors", refer to the primary mTOR inhibitor, rapamycin itself, and also to related compounds such as and various related compounds, such as temsirolimus, everolimus, torin-1, torin-2, WYE-354, and metformin, which may have similar activity.

As used herein, "effective amount" or "therapeutically effective amount" of an mTOR inhibitor, such as rapamycin, refers to a sufficient amount of inhibitor to perform an intended task and achieve an intended result. For example, a therapeutically effective amount of rapamycin may be an amount which is sufficient to treat a particular target indication, e.g. keratinocyte hyperproliferation or other condition for which an mTOR inhibitor can be used. It is understood that various biological factors may affect the ability of a particular agent to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

The terms, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, the term "substantially free of" as it refers to the presence or lack of a particular composition or ingredient or component in a given formulation refers to the complete or near complete absence of the ingredient from the formulation such that the ingredient, if present, forms only a minor component or impurity of the formulation. When the phrase "substantially free of" refers compounds, separate from the solvent, that solvate the mTOR inhibitor, the amount of the component present should not solubilize an amount of the mTOR inhibitor so as to negatively impact the therapeutic effect of the formulation.

As used herein, the term "about" is used to provide flexibility to a numerical range endpoint by providing that a given value may be "a little above" or "a little below" the endpoint.

As used herein, compounds, formulations, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

mTOR inhibitors are a potent class of pharmaceutically active agents that can be useful in treating a variety of conditions. There is a need that exists in the marketplace for topical formulation for delivering mTOR inhibitors. Formulations for mTOR inhibitors can be challenging because of their structures and solubility challenges that exist for many of these compounds. For example, rapamycin has intermediate polarity and is therefore poorly solubilized in aqueous compositions, ethanolic compositions, triglycerides, alkanes, and silicone systems. Benzyl alcohol has been identified as a solvent that can effectively solubilize rapamycin. In particular, benzyl alcohol can support 20 wt % solutions and higher of rapamycin. However, benzyl alcohol does not conveniently form stable emulsions above 10 wt % loading of benzyl alcohol using typical pharmaceutical surfactants. For example, formulations utilizing Span 80 and/or Tween 20 as surfactants were only able to achieve benzyl alcohol loading of 20 wt % or less. Further, emulsions made with Span 80 and/or Tween 20 demonstrated poor stability with room temperature overnight storage producing 5% separation with discrete coalesced droplets visible.

With the above in mind, a stable and effective transdermal formulation for delivering mTOR inhibitors, such as rapamycin, has been developed by the present inventors and is described herein. In particular, the present invention provides formulations and compositions for the transdermal delivery of mTOR inhibitors. In one embodiment a formulation for transdermally delivering mTOR inhibitors may include a therapeutically effective amount of the mTOR inhibitor, such as rapamycin, a polymer having surfactant properties, a polymer having thickening properties, a solvent for solubilizing the mTOR inhibitor, a glycol, a $C_{10}$-$C_{20}$ fatty acid; and a base. In one embodiment, a formulation for topical application of rapamycin is provided which include rapamycin, a polymer having surfactant properties, a polymer having thickening properties, benzyl alcohol, a glycol, a $C_{10}$-$C_{20}$ fatty acid; and a base. In a further embodiment, a formulation for transdermally delivering rapamycin can include about 55 wt % to about 98 wt % water, about 0.1 wt % to about 8.0 wt % rapamycin, about 0.05 wt % to about 0.5 wt % of a polymer having surfactant properties, about 0.4 wt % to about 1.0 wt % of a polymer having thickening properties, about 0.5 wt % to about 4.0 wt % of a glycol, about 1 wt % to about 40 wt % of benzyl alcohol, about 0.2 wt % to about 2.5 wt % of a $C_{10}$-$C_{20}$ fatty acid, and about 0.1 wt % to about 0.5 wt % of a base.

The amount of mTOR present in the formulation can vary depending on the particular mTOR inhibitor being used. In one embodiment, the formulation can include from 0.1 wt % to about 20 wt % of mTOR inhibitor. In another embodiment, the mTOR inhibitor can comprise about 0.5 wt % to about 10 wt % of the formulation. In another embodiment, the mTOR inhibitor can comprise about 0.5 wt % to about 8 wt %. In another embodiment, the mTOR inhibitor can comprise about 0.5 to about 5 wt %. In still a further embodiment, the mTOR inhibitor can comprise about 0.5 to about 3 wt %. In one embodiment, the mTOR inhibitor can comprise 0.5 wt % to about 2 wt % of the formulation. In still a further embodiment, the mTOR inhibitor can comprise about 1 wt % of the formulation. In some embodiments, the formulations of the present invention can include rapamycin as the mTOR inhibitor and can be present in an amount of from about 0.1 wt % to about 10 wt % of the formulation. In one embodiment the mTOR inhibitor can be rapamycin and can comprise 0.5 wt % to about 8 wt %. In another embodiment, the mTOR inhibitor can be rapamycin and can comprise about 0.5 wt % to about 4 wt % of the formulation. In still a further embodiment, the mTOR embodiment can be rapamycin and can comprise about 0.5 wt % to about 3 wt % of the formulation. In another embodiment, the mTOR inhibitor can be rapamycin and can comprise about 0.5 wt % to about 1.5 wt % of the formulation.

Polymers having surfactant properties (surfactant polymers) can include a wide array of surfactant or emulsifying polymers that are known in the art. Non-limiting examples of polymers having surfactant or emulsifying properties include, but are not limited to hydrophobically modified polyacrylic acid commercially under the tradename Pemulen™ TR-I and TR-2 by Lubrizol Corp., water-soluble or water-swellable copolymers based on acrylamidoalkyl sulfonic acid and cyclic N-vinylcarboxamides commercially available under the tradename Aristoflex® AVC by Clariant Corporation; water-soluble or water-swellable copolymers based on acrylamidoalkyl sulfonic acid and hydrophobically modified methacrylic acid commercially available under the tradename Aristoflex® HMB by Clariant Corporation and a homopolymer of acrylamidoalkyl sulfonic acid commercially available under the tradename Granthix APP by Grant Industries, Inc. Another class of notable polymeric emulsifier includes hydrophobically-modified, crosslinked, anionic acrylic copolymers, including random polymers, but may also exist in other forms such as block, star, graft, and the like. In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least about 3 carbon atoms.

Other materials that may be suitable polymeric surfactants can include ethylene oxide/propylene oxide block copolymers, sold under the trade name PLURONIC®, available from BASF Corporation of Parsippany, N.J., modified cellulose polymers such as those modified cellulose polymers described by the trade name KLUCEL®, available from Hercules Corporation of Wilmington, Del. Particularly notable embodiments of the invention are compositions that include hydrophobically modified polyacrylic acid, acrylamidoalkyl sulfonic acid, cyclic N-vinylcarboxamides, acrylamidoalkyl sulfonic acid, hydrophobically modified methacrylic acid, a homopolymer of acrylamidoalkyl sulfonic acid, or combinations thereof as polymeric emulsifiers; and monomeric anionic surfactants, monomeric amphoteric surfactants, or combinations thereof as foaming agents. More particularly notable embodiments of the invention are compositions that include hydrophobically modified polyacrylic acid; water-soluble or water-swellable copolymers based on acrylamidoalkyl sulfonic acid, cyclic N-vinylcarboxamides; water-soluble or water-swellable copolymers based on acrylamidoalkyl sulfonic acid, hydrophobically modified methacrylic acid; a homopolymer of acrylamidoalkyl sulfonic acid, or combinations thereof as polymeric emulsifiers, and include a betaine as the foaming surfactant. Especially notable embodiments of the invention are compositions that include copolymers based on acrylamidoalkylsulfonic acids and cyclic N-vinylcarboxamides and/or linear N-vinylcarboxamides (e.g., Aristoflex® AVC and Aristoflex® HMB from Clariant Corporation) as polymeric emulsifiers and a betaine as foaming surfactant.

Polymers having surfactant properties can enhance the ability of a formulation to support highly loaded emulsions of low polarity oils, and it has been discovered that it is in some circumstances possible to extend this capability to form emulsions of an intermediate polarity material such as benzyl alcohol. The common practices of predispersing surfactant polymers in a non-aqueous dispersed phase (i.e. benzyl alcohol) phase or co-dispersing the surfactant polymer with an oil phase into an aqueous phase were tried but were not capable of producing stable emulsions. Rather, the benzyl alcohol phase wetted the surfactant polymer powder and then plasticized the polymer, creating "gummy" lumps that showed no tendency to solubilize in the continuous aqueous phase, even with extended stirring of many hours. In an attempt to create a stable emulsion, it was discovered that the surfactant polymer material can be fully pre-dispersed and solubilized in an aqueous phase before any benzyl alcohol was dispersed into the solution. This substantially prevented or avoided formation of the gummy lumps that otherwise formed with the conventional procedure described above. In some embodiments, the surfactant polymer can comprise about 0.01 wt % to about 3 wt %. In one embodiment, the surfactant polymer can comprise about 0.1 wt % to about 1.0 wt % of the formulations of the present invention. In one embodiment, the surfactant polymer can comprise about 0.1 wt % to about 0.5 wt % of the total formulation. In another embodiment, the surfactant polymer can comprise about 0.15 wt % to about 0.3 wt % of the total formulation.

Without wishing to be bound to a particular theory, it is understood that low-polarity oil phases typical of topical formulations, such as alkanes, triglycerides, and silicones, may be readily dispersed by a polymer having surfactant properties as described above. However, it is understood the intermediate polarity of benzyl alcohol imparts a tendency to plasticize the dry polymer. It has been discovered that it is advantageous to dissolve the polymer fully in the aqueous phase prior to dispersion of the benzyl alcohol phase.

The formulations of the present invention also can include a polymer having thickening properties (thickening polymer). In one embodiment, the polymer having thickening properties can be a hydrophobically modified cross-linked acrylate copolymer (Carbopol® Ultrez 20). Other polymers having similar properties may also be used. Non-limiting examples of polymers having thickening properties can include PEG-150 distearate, PEG-7 glyceryl cocoate, PEG-200 hydrogenated glyceryl palmitate, PEG-120 methyl glucose dioleate, carboxymethylene polymer, carboxyvinyl polymer, acrylates, $C_{10}$-$C_{30}$ alkyl acrylate crosspolymers, and combinations thereof. In some embodiments, the polymer having thickening properties can comprise about 0.1 wt % to about 3 wt %. In another embodiment, polymers having thickening properties can be present in amounts of 0.4 wt % to about 1.0 wt % of the total composition. In one embodiment, the polymer having thickening properties comprises about 0.5 wt % to about 0.75 wt % of the total composition. The thickening polymer can be mixed with the surfactant polymer and water as a component of an aqueous phase.

Thickening polymers such as those described herein may contribute qualities to the formulation beyond merely altering the rheology of the continuous phase. In the case that the thickening polymers exhibit solubility or plasticization of benzyl alcohol, the primary drug solvent, such polymers may influence both the solubilization of the drug to be delivered and/or the thermodynamic chemical potential of the drug and solvent system, altering the drug delivery characteristics of the formulation by a variety of related effects. Such effects can include but are not limited to: changing the evaporation rate of the drug solvent; changing the solubility limit of the drug in the solvent system, changing the solubility of the drug-solvent system in skin, changing the physical characteristics (for example freezing point) of the drug-solvent system or the continuous phase, among others. In the present composition, most preferably the polymers are selected to interact minimally with the drug-solvent system, maximizing the chemical potential of that system so as to promote rapid percutaneous delivery of the drug.

In some embodiments, the formulations of the present invention can also include a base or buffer system, which is present in the formulation to neutralize and/or activate the thickening polymer in order to facilitate the formation of a composition having the desirable rheological qualities. Any base or buffer system known in the art and suitable for use in a skin contact application can be used. In one embodiment, the base can include triethanolamine, such as solutions of 10% triethanolamine (TEA), tetrasodium ethylenediaminetetraacetic acid (EDTA), alkali metal hydroxides like sodium hydroxide (NaOH), salts of weak acids such as ammonium lactate, sodium citrate, sodium ascorbate, or mixtures thereof. The base component also provides utility in that the pH of the overall composition may be adjusted to a range favorable for minimizing irritation of the skin due to pH effects. In some embodiments formulations of the present invention can also include an acid or the acid component of a buffer system, and any acid known in the art and appropriate for human skin contact may be used. Examples of acids useful in the present formulation and commonly used to adjust pH of topical formulations include but are not limited to: citric acid, lactic acid, ascorbic acid, and hydrochloric acid, and combinations of these and similar acids. Generally the pH of the formulations of the present invention can be between about 5.0 and about 7.0.

In one embodiment, the base can be a 10% solution of triethanolamine and the thickening polymer can be Carbopol® Ultrez 10 and the ratio (w/w) of TEA solution to Carbopol® polymer can be about 0.46:1. Addition of as much as 0.6:1 TEA to Carbopol® results in rapid and substantial breakage of the emulsion. The emulsion is highly sensitive to pH with the addition of base sometimes resulting in local increases of viscosity or "hot spots" of lower pH that are prone to emulsion breakage. Accordingly, it can be useful to introduce the benzyl alcohol phase (rapamycin and benzyl alcohol) after the addition of the base of the aqueous composition of the polymers, water, glycol and fatty acid. By doing this preparation of a fresh sample of the formulated cream is also simplified, because a freshly prepared rapamycin/benzyl alcohol solution aliquot may be added as a single component to a container in which another single component, the aqueous mixture of polymer, glycol, fatty acid and base, is pre-dispensed. The two components can then be mixed. This is particularly effectively accomplished by use of a "Flacktek" centrifugal mixer, similar to dental amalgam mixers, which is of particular utility in dispersing mixtures of high viscosity.

The formulations of the present invention can also include a glycol and/or glycol ether. Non-limiting examples of glycols and glycol ethers can be selected from butylene glycol, propylene glycol, diethylene glycol (Transcutol), triethylene glycol, ethylene glycol monomethyl ether, or other glycols and glycol ethers, and combinations thereof. The formulations can also include a $C_{10}$-$C_{20}$ fatty acid. Non-limiting examples of $C_{10}$-$C_{20}$ fatty acid can include oleic acid, arachidonic acid, linoleic acid, linolenic acid, or other fatty acids or combinations of fatty acids, and preferably unsaturated cis conformation fatty acids. Without being bound to any particular interpretation, such conformations are understood to disrupt superficial packing of the structured lipids of the stratum corneum, thereby promoting fluidization of these lipids and thus enhancing the diffusion of the drug and/or solvent into the skin, and are believed to play this role in the present formulation. In one embodiment, the $C_{10}$-$C_{20}$ fatty acid can be oleic acid. The presence of glycol and/or fatty acid components in formulations with benzyl alcohol emulsions can sometimes result in localized breakage of the emulsion, which is less than ideally robust at higher loadings (e.g. 25% or higher). It has been discovered that to avoid some of these problems it can be advantageous to add the glycol or fatty acid to the aqueous surfactant polymer phase (with water) in order to fully dissolve the glycol and disperse the fatty acid in the aqueous polymer phase prior to addition of the benzyl alcohol.

The presence of benzyl alcohol in the formulations facilitates the solubility of the rapamycin. The benzyl alcohol can comprise about 1 wt % to about 40 wt % of the formulation. In one embodiment, the benzyl alcohol can comprises about 5 wt % to about 30 wt % of the formulation. In another embodiment, the benzyl alcohol can comprise about 10 wt % to about 27 wt % of the formulation. When the rapamycin is added to the benzyl alcohol the rapamycin is solubilized in the benzyl alcohol. In one embodiment, the benzyl alcohol and the rapamycin collectively can comprise about 25 wt % to about 32 wt % of the formulation. In one embodiment, the formulations of the present invention can be free of components that solubilize rapamycin outside benzyl alcohol.

In some embodiments, the formulations of the present invention can also include an emollient component, for example mineral oil, dimethicone, or combinations thereof. The emollient component may provide multiple advantages, which include but are not limited to improving the cosmetic feel and appearance of the formulation during application and after drying. A wide range of emollient additives are known in the art and any of these may be included in the present compositions. Generally, inclusion of emollient materials is understood by those versed in the art to suppress evaporation rate and to reduce the chemical potential of the drug-solvent system in regard to percutaneous absorption. Surprisingly, the inclusion of either mineral oil or dimethicone in the composition of the present invention did not reduce delivery of the mTOR inhibitor in mouse or human skin.

Many emollients are co-soluble with the benzyl alcohol drug solvent and particular emollients may be selected to influence the delivery characteristics of the composition. For example, triglycerides are soluble in benzyl alcohol and will thereby reduce the evaporation rate and the chemical potential of the drug-solvent system in regard to percutaneous absorption. Without wishing to be bound to any particular interpretation, it is believed that because mineral oil and dimethicone are poorly miscible with benzyl alcohol, such dilution effects upon drug delivery performance were circumvented. It is also believe that the tendency of mineral oil and silicone to form a barrier-like film on the skin surface helps to promote percutaneous absorption in the manner analogous to the effect of an occlusive dressing, well known to improve topical delivery of some drugs. Accordingly, in some embodiments, the formulation can include emollient materials that are poorly miscible with the solvent for solubilizing the mTOR inhibitor. In product testing, inclusion of such immiscible emollients further provided improved cosmetic feel and also prevented formation of a visible powdery residue of the polymeric components, believed to be because of simple wetting of the residual powder by the emollient component. Formulations produced without inclusion of these immiscible emollients left a distinct visible white powdery deposit.

In one aspect the formulations of the present invention can be in the forms of aqueous lotions or creams. The formulations can be such that following application to a skin surface, the skin surface is dry, or substantially dry, to the touch within about 1 minute to about 5 minutes. In one embodiment, the following application of the formulation to a skin surface, the skin surface is dry, or substantially dry, to the touch within about 1 minute to about 2 minutes. In another embodiment, following application of the formulation to a skin surface, the skin surface is dry, or substantially dry, to the touch in less than about 1 minute. In one embodiment, the formulation of the present invention can be substantially free of triglycerides, waxes or liquid surfactants that, following application to a skin surface and allowed to dry, are left behind on the skin surface (i.e. leave a residue). Following drying, the formulations of the present disclosure typically do not leave a residue on the skin surface. This is advantageous in that the risk of transfer of the substances, particularly the rapamycin, from the skin is significantly reduced as compared to other non-aqueous formulations (e.g. ointments). Further, by reducing superficial residue on the skin surface, the presence of materials that might solubilize rapamycin locally at the skin surface without assisting their transport into the skin is reduced, which tendency might otherwise act to compromise the efficacy of the composition. For instance, if a triglyceride residue remained at the surface of the skin while the other components evaporated or absorbed into the skin, the residual triglyceride would be likely to dissolve a fraction of the rapamycin active ingredient, which would therefore be less available to be delivered by the percutaneous absorbing portions of the formulation, as topically applied triglycerides are not understood to penetrate significantly into the skin.

The compositional make-up of the formulations disclosed herein can be such that they have a low yield value, which allows it to be readily applied to sensitive skin areas without requiring substantial pressure for rubbing or spreading. Nonetheless, the yield value of the compositions is still high enough to provide for convenient, localized, and non-messy application. This is particularly advantageous in that many conditions that can be treated with formulations of the present invention often result in tender or sensitive skin. Accordingly, the formulations of the present invention can provide for better patient compliance.

EXAMPLES

The following examples are provided to promote a more clear understanding of certain embodiments of the present invention, and are in no way meant as a limitation thereon. The compositions may be suitably modified by a person skilled in the art.

Example 1—Production of a Rapamycin Delivery Formulation A formulation for transdermal delivery of rapamycin can include the compositions as set forth in Table I:

TABLE I

| Phase | Component | Manufacturer | INCI | Concentration | Fraction | Mass | Running mass |
|---|---|---|---|---|---|---|---|
| A | WFI | Calbiochem | Water for Injection | 100% | 65.05% | 13.010 | 13.010 |
| A | Pemulen™ TR-1 or TR-2 | Lubrizol Corp | Acrylates/C10-30 Alkyl Acrylate Crosspolymer | 100% | 0.24% | 0.048 | 13.058 |
| A | Carbopol® Ultrez 10 or 20 | Lubrizol Corp | Acrylates/C10-30 Alkyl Acrylate Crosspolymer | 100% | 0.66% | 0.132 | 13.190 |
| B | Butylene Glycol or propylene glycoll | Spectrum Chemicals | Butylene Glycol | 100% | 2.50% | 0.500 | 13.690 |
| B | Oleic Acid | Spectrum Chemicals | Oleic Acid | 100% | 1.25% | 0.250 | 13.940 |
| C | Benzyl Alcohol | Spectrum Chemicals | Benzyl Alcohol | 100% | 24.00% | 4.800 | 18.490 |
| C | Rapamycin API | LC Labs | Rapamycin | 100% | 6.00% | 1.200 | 15.140 |
| D | Triethanolamine | Spectrum Chemicals | Triethanolamine | 10% | 0.30% | 0.060 | 15.200 |

Example 2—Rapamycin Delivery Formulation

A formulation for topical application/transdermal delivery of rapamycin can include the compositions as set forth in Table II:

TABLE II

| INGREDIENTS | AMOUNT (wt %) | FUNCTION |
|---|---|---|
| Rapamycin | 1.0 | mTOR Inhibitor |
| Benzyl Alcohol | 4.0 | Solvent for solubilizing mTOR |
| Propylene Glycol | 2.9 | Permeation Enhancer |
| Oleic Acid | 1.4 | Permeation Enhancer |
| Mineral Oil | 1.0 | Emollient |
| Carbopol® Ultrez 10 | Collectively 1% | Reheology Modifier (polymer thickener) |
| Pemulen™ TR-1 | | Emulsifier (polymer surfactant) |
| Triethanolamine | 0.03 | pH adjustment |
| Water for Injection | q.s. | Vechiel |

Example 3—Production of a Rapamycin Delivery Formulation

A formulation for transdermal delivery of rapamycin is prepared utilizing the compositions set forth in Table I or II and in accordance with the steps described below. A container is provided containing the water of Phase A and stirring is commenced to the level of a rapid vortex but below cavitation. The polymers of Phase A, Pemulen™ (TR-1 or TR-2) and Carbopol® Ultrez (Ultrez 10 or 20) are added to the stirring water slowly to avoid dusting or clumping. The phase A composition thus far prepared is stirred at high speed (>400 rpm for magnetic stirrer) until the polymers are completely dissolved. The stirring of the Phase A compositions are maintained and the components of Phase B, butylene glycol and oleic acid, are added to the mixture of Phase A and mixed thoroughly. It is noteworthy that the Phase A, or the mixture of Phase A and Phase B together can be stored under refrigeration or preserved until needed for mixing with Phase C. The components of Phase C, namely benzyl alcohol and rapamycin, can be added to a rapidly stirred mixture of Phases A and B and allowed to mix on high speed (e.g. 1000 rpm) for longer than 5 minutes. Phase D can then be added to the resulting mixture of Phases A-C. The resultant composition can be used immediately or can be placed in a closed container and stored at 1-10° C. until ready for use.

In certain embodiments where Phase A and B are prepared and stored until mixing with the other phases, the mixture of Phases A and B (as prepared above) can be mixed with Phases C and D. Phase C is a mixture of rapamycin and benzyl alcohol in the relative proportions to each other as shown in Table I (4:1—benzyl alcohol to rapamycin). The mixture of Phases A and B is mixed with Phases C and D in the relative proportions as shown in Table III.

TABLE IIII

| Contains | Percent of total | Mass for typical 1 g micro-batch |
|---|---|---|
| Phase A + B above | 67% | 0.6700 |
| Phase C(Rapamycin/BenzylOH) | 30% | 0.3000 |
| Phase D TEA 10% (D above) | 3% | 0.0300 |

The composition can be prepared by mixing the mixture of Phases A and B with Phase C in a container. The resultant mixture can be mixed with shear to form a milky white emulsion of homogeneous appearance. Phase D can then be added and the composition mixed thoroughly. The final composition can be used immediately or can be placed in a closed container and stored at 1-10° C. until ready for use.

Example 4—Evaluation of Benzyl Alcohol as Solvent for Topical mTOR Formulation

To evaluate whether benzyl alcohol has deleterious effects on rapamycin activity, rapamycin was dissolved in benzyl alcohol (and compared with other solvents as indicated) and evaluated for its ability to block phosphorylation of ribosomal protein S6, a commonly used method to assess mTOR pathway inhibition by rapamycin, in human HaCaT and patient-derived keratinocytes. As shown in FIG. 1A, the rapamycin dissolved in benzyl alcohol or other commonly-used solvents including DMSO, ethanol and diglycol efficiently inhibits ribosomal protein S6 phosphorylation (P-S6) with little or no effect on total S6 protein levels. In the assays described below, a P-S6-specific antibody recognizes only the phosphorylated form of S6 whereas the other antibody recognizes total S6 protein (i.e., both P-S6 and unphosphorylated S6). Similar inhibition of S6 phosphorylation relative to total S6 protein was seen in PC patient-derived keratinocytes (grown from a biopsy) treated with rapamycin (data not shown). Topical formulations, with or without rapamycin dissolved in benzyl alcohol, were administered to mouse skin including ears and demonstrated to decrease S6 phosphorylation, albeit to a lesser extent than seen in tissue culture cells. The inhibition of phospho-S6 was observed by both western blot analysis of protein extracts from treated mouse skin (FIG. 1B) and by immunohistochemistry (IHC) of frozen sections prepared from treated mouse skin (FIG. 1C-F). These studies indicate that, as expected, S6 phosphorylation is inhibited relative to total S6 protein following topically-administered rapamycin, indicating that the topical formulation is allowing delivery of drug through the skin barrier. Furthermore, in gross examination of topically-treated mouse ears, flanks and footpads, no changes were observed compared to untreated or placebo-treated skin, suggesting little or no irritation (data not shown).

Example 5—Effect of mTOR Inhibitors on Ribosomal Protein

Next-generation mTOR inhibitors have similar effects on ribosomal protein S6-phosphoylation (p-S6) when compared to rapamycin. Human HaCaT keratinocytes growing in serum ("Serum") were treated with rapamycin or the other indicated mTOR inhibitors for the indicated times and then subjected to western blot analysis (Top) as in FIG. 2A. Also shown are keratinocytes that were serum-starved (ss) for 14 hours. These results indicate that serum starvation or treatment with mTOR inhibitors has a similar effect on S6 phosphorylation. The p-S6 levels were quantified and the ratio of p-S6 to total S6 (total S6 data not shown) was graphed in FIG. 2B in similar fashion to FIG. 1. Inhibition of S6 phosphorylation indicates that the mTOR pathway has been inhibited as S6 phosphorylation is downstream of mTOR, the target of rapamycin.

Example 6—Rapamycin Distribution in Human Explant Skin 16 Hours after Application of Rapamycin Formulation To test delivery of rapamycin from a formulation similar to that disclosed in Example 2, the formulation was applied to explant human skin. FIG. 3 shows the depth profile analysis of the distribution of rapamycin upon topical delivery into human skin, demonstrating rapamycin concentrations present within the epidermis (and dermis) well above the IC50 value required to inhibit S6 phosphorylation in cell culture. This testing demonstrates the efficacy of the disclosed formulations.

It should be understood that the above-described various types of compositions, are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

The invention claimed is:

1. An oil in water emulsion formulation for transdermal delivery of an mTOR inhibitor, comprising:
   the mTOR inhibitor selected from the group consisting of rapamycin, temsirolimus, everolimus, AP-23573, torin-1, torin-2, WYE-354, metformin, and combinations thereof;
   a polymer having surfactant properties comprising a hydrophobically modified polyacrylic acid;
   a polymer having thickening properties comprising a hydrophobically modified cross-linked acrylate copolymer;
   a solvent for solubilizing the mTOR inhibitor selected from the group consisting of benzyl alcohol, DMSO, ethanol, diglycol, and combinations thereof;
   a glycol;
   a $C_{10}$-$C_{20}$ fatty acid;
   water;
   triethanolamine; and
   an emollient selected from the group consisting of mineral oil, dimethicone, and combinations thereof, wherein the oil in water emulsion is a lotion or cream.

2. The formulation of claim 1, wherein the polymer having surfactant properties comprises about 0.1 wt % to about 0.5 wt % of the total composition.

3. The formulation of claim 1, wherein the polymer having surfactant properties comprises about 0.15 wt % to about 0.3 wt % of the total composition.

4. The formulation of claim 1, wherein the polymer having thickening properties comprises about 0.4 wt % to about 1.0 wt % of the total composition.

5. The formulation of claim 1, wherein the polymer having thickening properties comprises about 0.5 wt % to about 0.75 wt % of the total composition.

6. The formulation of claim 1, wherein the solvent for solubilizing the mTOR inhibitor comprises about 0.5 wt % to about 40 wt % of the formulation.

7. The formulation of claim 1, wherein the solvent for solubilizing the mTOR inhibitor comprises about 1 wt % to about 10 wt % of the formulation.

8. The formulation of claim 1, wherein the solvent for solubilizing the mTOR inhibitor comprises about 1 wt % to about 7 wt % of the formulation.

9. The formulation of claim 1, wherein the solvent for solubilizing the mTOR inhibitor is benzyl alcohol.

10. The formulation of claim 9, wherein the benzyl alcohol comprises 1 wt % to 7 wt % of the formulation.

11. The formulation of claim 1, wherein the mTOR inhibitor is rapamycin.

12. The formulation of claim 9, wherein the benzyl alcohol comprises 1 wt % to 10 wt % of the formulation.

13. The formulation of claim 1, wherein the mTOR inhibitor comprises about 0.1 wt % to about 10.0 wt % of the formulation.

14. The formulation of claim 1, wherein the mTOR inhibitor comprises about 0.5 wt % to about 8 wt % of the formulation.

15. The formulation of claim 1, wherein the mTOR inhibitor is rapamycin and the rapamycin comprises about 0.5 wt % to about 5 wt % of the formulation.

16. The formulation of claim 1, wherein the mTOR inhibitor is rapamycin and the rapamycin comprises about 0.5 wt % to 3 wt % of the formulation.

17. The formulation of claim 1, wherein the $C_{10}$-$C_{20}$ fatty acid is oleic acid, arachidonic acid, linoleic acid, linolenic acid, or combinations thereof.

18. The formulation of claim 1, wherein the glycol is selected from the group consisting of butylene glycol, propylene glycol, diethylene glycol, triethylene glycol, ethylene glycol monomethyl ether, and combinations thereof.

19. The formulation of claim 1, wherein the solvent for solubilizing the mTOR inhibitor solubilizes the mTOR inhibitor in the formulation and the formulation is substantially free of other components that solubilize mTOR inhibitor.

20. The formulation of claim 1, wherein the benzyl alcohol and the rapamycin collectively comprise about 2 wt % to about 10 wt % of the formulation.

21. The formulation of claim 1, wherein, following application to a skin surface, the formulations is dry to the touch within about 1 minute to about 5 minutes.

22. The formulation of claim 1, wherein, following application to a skin surface, the formulations is dry to the touch within about 1 minute to about 2 minutes.

23. The formulation of claim 1, wherein, following application to a skin surface, the formulations is dry to the touch in less than about 1 minute.

24. The formulation of claim 1, wherein the formulation is substantially free of triglycerides, waxes or liquid surfactants that, following application to a skin surface and allowed to dry, are left behind on the skin surface.

25. The formulation of claim 1, wherein the formulation is a lotion.

26. An oil in water emulsion for transdermal delivery of rapamycin, comprising:
   55 wt % to about 98 wt % water;
   0.1 wt % to about 3 wt % rapamycin;
   0.05 wt % to about 1.0 wt % of a polymer having surfactant properties comprising a hydrophobically modified polyacrylic acid;
   0.4 wt % to about 1.0 wt % of a polymer having thickening properties comprising a hydrophobically modified cross-linked acrylate copolymer;
   0.5 wt % to about 4 wt % of a glycol;
   1 wt % to about 10 wt % of benzyl alcohol;
   0.2 wt % to about 2.5 wt % of a $C_{10}$-$C_{20}$ fatty acid;
   0.01 wt % to about 0.5 wt % of a 10% aqueous solution of triethanolamine; and
   an emollient selected from the group consisting of mineral oil, dimethicone, and combinations thereof, wherein the oil in water emulsion is a lotion or cream.

27. The formulation of claim 1, wherein the triethanolamine is a 10% aqueous solution of triethanolamine.

28. The formulation of claim 27, wherein the polymer having thickening properties is a hydrophobically modified cross-linked acrylate copolymer and the weight/weight ratio of triethanolamine to the hydrophobically modified cross-linked acrylate copolymer is about 0.46:1.

29. An oil in water emulsion for transdermal delivery of rapamycin, comprising:
   about 65.05% water;
   about 0.24% of a hydrophobically modified polyacrylic acid;
   about 0.66% of a hydrophobically modified cross-linked acrylate copolymer;
   about 2.5% Butylene glycol or propylene glycol;
   about 1.25% oleic acid;
   about 24% benzyl alcohol;
   about 6% of Rapamycin; and
   about 0.3% of a 10% aqueous solution of triethanolamine,
   wherein the oil in water emulsion is a lotion or cream.

30. An oil in water emulsion for transdermal delivery of rapamycin, comprising:
   about 1 weight % collectively of a hydrophobically modified cross-linked acrylate copolymer and a hydrophobically modified polyacrylic acid;
   about 2.9 weight % propylene glycol;
   about 1.4 weight % oleic acid;
   about 4 weight % benzyl alcohol;
   about 1 weight % of Rapamycin;
   about 0.03 weight % of triethanolamine;
   about 1 weight % mineral oil and
   about 86.6 weight % water,
   wherein the oil in water emulsion is a lotion or cream.

* * * * *